US011930854B2

(12) United States Patent
Jeong et al.

(10) Patent No.: US 11,930,854 B2
(45) Date of Patent: Mar. 19, 2024

(54) ELECTRONIC VAPORIZER THAT IS COUPLABLE TO AN ELECTRONIC DEVICE

(71) Applicant: KT&G CORPORATION, Daejeon (KR)

(72) Inventors: Eun Mi Jeong, Daejeon (KR); Dong Kyun Ko, Sejong (KR); Ji Hun Yang, Sejong (KR); In Su Park, Seoul (KR); Soon Hwan Jung, Daejeon (KR)

(73) Assignee: KT&G CORPORATION, Daejeon (KR)

( * ) Notice: Subject to any disclaimer, the term of this patent is extended or adjusted under 35 U.S.C. 154(b) by 792 days.

(21) Appl. No.: 17/040,219

(22) PCT Filed: Jul. 11, 2019

(86) PCT No.: PCT/KR2019/008543
§ 371 (c)(1),
(2) Date: Sep. 22, 2020

(87) PCT Pub. No.: WO2020/017822
PCT Pub. Date: Jan. 23, 2020

(65) Prior Publication Data
US 2021/0015159 A1    Jan. 21, 2021

(30) Foreign Application Priority Data

Jul. 19, 2018    (KR) .......................... 10-2018-0084192

(51) Int. Cl.
*A24F 40/50*    (2020.01)
*A24F 40/44*    (2020.01)

(52) U.S. Cl.
CPC .............. *A24F 40/50* (2020.01); *A24F 40/44* (2020.01)

(58) Field of Classification Search
CPC .......... A24F 40/50; A24F 40/40; A24F 40/44; A24F 40/10; A24F 40/485
See application file for complete search history.

(56) References Cited

U.S. PATENT DOCUMENTS 9,282,772 B2 *   3/2016   Tucker ..................... H05B 3/16
9,623,205 B2     4/2017   Buchberger
(Continued)

FOREIGN PATENT DOCUMENTS

CN    103781375 A    5/2014
CN    103917119 A    7/2014
(Continued)

OTHER PUBLICATIONS

Extended European Search Report dated Mar. 11, 2022 in European Application No. 19838474.5.
(Continued)

*Primary Examiner* — Hae Moon Hyeon
(74) *Attorney, Agent, or Firm* — Sughrue Mion, PLLC

(57) ABSTRACT

An electronic vaporizer for generating an aerosol includes a housing to be installed to an electronic device by being coupled to the electronic device through a connecting interface of the electronic device, and including: a connecting interface that receives power from a battery included in the electronic device when coupled to the connecting interface of the electronic device, a liquid storage for storing a liquid aerosol generating material and supplying the liquid aerosol generating material to a wick when the housing is disposed in a predetermined posture, an atomizer that includes a wick and a heater for generating an aerosol by heating the liquid aerosol generating material supplied to the wick, and a control circuit that controls heating of the heater for generating the aerosol, based on the power supplied from the battery.

12 Claims, 11 Drawing Sheets

(56) References Cited

U.S. PATENT DOCUMENTS

| | | | |
|---|---|---|---|
| D799,746 S * | 10/2017 | Leidel | D27/163 |
| 9,894,938 B2 | 2/2018 | Vick et al. | |
| 10,412,997 B2 * | 9/2019 | Cameron | H04W 4/12 |
| 10,835,693 B2 * | 11/2020 | Klurfeld | G04B 47/00 |
| 10,842,194 B2 | 11/2020 | Batista | |
| 11,026,448 B2 | 6/2021 | Leadley et al. | |
| 11,043,778 B2 * | 6/2021 | Cipully | H01R 13/70 |
| 11,229,236 B1 * | 1/2022 | Arnel | A24F 40/40 |
| 2013/0319438 A1 * | 12/2013 | Liu | A24F 40/485 |
| | | | 131/329 |
| 2014/0202454 A1 | 7/2014 | Buchberger | |
| 2014/0202472 A1 | 7/2014 | Levitz et al. | |
| 2015/0080053 A1 | 3/2015 | Ciccarello et al. | |
| 2015/0215439 A1 | 7/2015 | Stanimirovic et al. | |
| 2016/0331035 A1 * | 11/2016 | Cameron | H04M 1/21 |
| 2017/0135410 A1 * | 5/2017 | Cameron | H01M 10/44 |
| 2017/0196270 A1 * | 7/2017 | Vick | H02J 7/0042 |
| 2017/0259170 A1 | 9/2017 | Bowen et al. | |
| 2017/0273358 A1 * | 9/2017 | Batista | A24F 40/40 |
| 2017/0303591 A1 * | 10/2017 | Cameron | H02J 7/342 |
| 2017/0360090 A1 * | 12/2017 | Grossfeld | H04M 1/72409 |
| 2018/0146711 A1 * | 5/2018 | Mazur | H05K 5/0017 |
| 2018/0160733 A1 | 6/2018 | Leadley et al. | |
| 2018/0160735 A1 * | 6/2018 | Borkovec | A24F 40/40 |
| 2019/0053540 A1 | 2/2019 | Baker et al. | |
| 2019/0281893 A1 * | 9/2019 | Valdez-Gibson | A24F 40/00 |
| 2019/0335814 A1 * | 11/2019 | Qiu | A24F 40/42 |
| 2019/0373952 A1 * | 12/2019 | Todd | A24F 40/40 |
| 2020/0022414 A1 * | 1/2020 | Leeds | H02J 7/0013 |

FOREIGN PATENT DOCUMENTS

| | | |
|---|---|---|
| CN | 106793835 A | 5/2017 |
| CN | 108135267 A | 6/2018 |
| EP | 3135134 A1 | 3/2017 |
| JP | 2014-521419 A | 8/2014 |
| JP | 2017-522876 A | 8/2017 |
| JP | 2018-502564 A | 2/2018 |
| KR | 10-2014-0101728 A | 8/2014 |
| KR | 101445113 B1 | 10/2014 |
| KR | 10-2014-0131298 A | 11/2014 |
| KR | 10-2016-0040442 A | 4/2016 |
| KR | 10-2017-0041680 A | 4/2017 |
| KR | 10-2018-0044410 A | 5/2018 |
| WO | 2013/050934 A1 | 4/2013 |
| WO | 2014/150573 A2 | 9/2014 |
| WO | 2016/023809 A1 | 2/2016 |
| WO | 2016/183002 A1 | 11/2016 |
| WO | 2017/055795 A1 | 4/2017 |
| WO | 2018/060675 A1 | 4/2018 |

OTHER PUBLICATIONS

Chinese Office Action dated Dec. 28, 2022 in Chinese Application No. 201980017711.0.

International Search Report for PCT/KR2019/008543, dated Oct. 18, 2019.

Notice of Reasons for Refusal dated Aug. 17, 2021 from the Japanese Patent Office in JP application No. 2020-551401.

* cited by examiner

ELECTRONIC VAPORIZER THAT IS COUPLABLE TO AN ELECTRONIC DEVICE

CROSS REFERENCE TO RELATED APPLICATIONS

This application is a National Stage of International Application No. PCT/KR2019/008543 filed Jul. 11, 2019, claiming priority based on Korean Patent Application No. 10-2018-0084192 filed Jul. 19, 2018.

TECHNICAL FIELD

The present disclosure relates to an electronic vaporizer, and specifically, to an electronic vaporizer that is coupled to an electronic device and capable of generating an aerosol.

BACKGROUND ART

An electronic vaporizer is a device that generates an aerosol by heating a liquid aerosol material by using a heater, and a user inhales the generated aerosol. A liquid aerosol generating material may be generated by mixing a complex composition composed of various fragrances and nicotine or fragrance combinations with a solvent of glycerin and propylene glycol. A liquid aerosol generating material is absorbed through a wick provided in the electronic vaporizer and a heater heats the absorbed material to generate an aerosol. In this case, a proper amount of liquid aerosol generating material needs to be supplied to a wick only when necessary. However, the liquid aerosol generating material may leak unintentionally, which causes inconvenience to a user carrying the electronic vaporizer.

Furthermore, an electronic vaporizer is generally provided with a battery for supplying power for operation of a heater. Particularly, most electronic vaporizers are equipped with a battery of a certain size and weight to ensure an appropriate number of puffs for the user. Thus, a weight of the battery accounts for a large portion of the total weight of an electronic device in the electronic vaporizer. Accordingly, this may cause a problem of poor portability of an electronic vaporizer.

DESCRIPTION OF EMBODIMENTS

Technical Problem

Various embodiments provide an electronic vaporizer that is coupled to an electronic device and capable of generating an aerosol. The technical problems to be solved by the present disclosure are not limited to the technical problems described above, and other technical problems may be inferred from the following embodiments.

Solution to Problem

According to one aspect, an electronic vaporizer for generating an aerosol includes a housing to be installed in an electronic device by being coupled to the electronic device through a connecting interface of the electronic device, and comprising: a connecting interface configured to receive power from a battery included in the electronic device when coupled to the connecting interface of the electronic device; a liquid storage configured to store a liquid aerosol generating material and supply the liquid aerosol generating material to a wick when the housing is disposed in a predetermined posture; an atomizer including the wick and a heater that generates the aerosol by heating the liquid aerosol generating material supplied to the wick; and a control circuit configured to control heating of the heater for generating the aerosol based on the power supplied from the battery.

In addition, the predetermined posture corresponds to a posture in which a user holds the electronic vaporizer above the electronic device while the electronic device and the electronic vaporizer are coupled to each other.

In addition, the liquid storage includes a connection path through which the liquid aerosol generating material is provided to the atomizer when the housing is disposed in the predetermined posture, and through which the liquid aerosol generating material is not provided to the atomizer when the housing is not disposed in the predetermined posture.

In addition, the control circuit monitors whether or not the connecting interface of the electronic device is coupled to the connecting interface of the housing, and controls the connection path to be opened when the connecting interfaces are coupled to each other, the control circuit, and controls the connection path to be closed when the connecting interfaces are not coupled to each other.

In addition, the housing further includes a mouthpiece provided on one side of the housing for a user to inhale the aerosol generated from the atomizer, and the mouthpiece provides the aerosol to the user when the housing is disposed in the predetermined posture.

In addition, the housing includes at least one hole for introducing external air into the housing; and an airflow path through which a mixture of the external air introduced through the hole and the generated aerosol is provided to the mouthpiece.

In addition, the housing further comprises a wireless communication module for establishing a wireless connection with the electronic device through wireless communication.

In addition, the wireless communication module receive data set in a vaporizer control application executed by the electronic device or transmits data requested from the vaporizer control application through the wireless connection established with the electronic device, and the control circuit controls operations of the electronic vaporizer under a control of the vaporizer control application.

In addition, the liquid storage includes one or more wall surfaces that partition an inner space of the liquid storage for storing the liquid aerosol generating material, and the one or more wall surfaces are disposed in a structure that provides the liquid aerosol generating material to the atomizer when the housing is disposed in the predetermined posture, and does not provide the liquid aerosol generating material to the atomizer when the housing is not disposed in the predetermined posture.

According to another aspect, an electronic vaporizer for generating an aerosol includes a connecting interface that receives power from a battery included in an electronic device when coupled to a connecting interface of the electronic device; a liquid storage for storing a liquid aerosol generating material and supplying the liquid aerosol generating material to a wick when the electronic vaporizer is disposed in a predetermined posture; an atomizer that includes a wick and a heater for generating an aerosol by heating the liquid aerosol generating material supplied to the wick; a control circuit that controls heating of the heater for generating the aerosol based on the power supplied from the battery; and a mouthpiece through which a user inhales the aerosol generated from the atomizer.

Advantageous Effects of Disclosure

According to above description, an electronic vaporizer may be coupled to an electronic device and driven by using a battery of the electronic device without a separate battery provided therein. Thus, the electronic vaporizer may be manufactured with a small volume and a light weight, and may be easily carried and kept by a user. In addition, an aerosol is generated only while the electronic vaporizer is disposed in a predetermined posture, and thus, leakage of the liquid aerosol generating material may be minimized during using, keeping, and carrying of the electronic vaporizer.

BEST MODE

Figure 1:
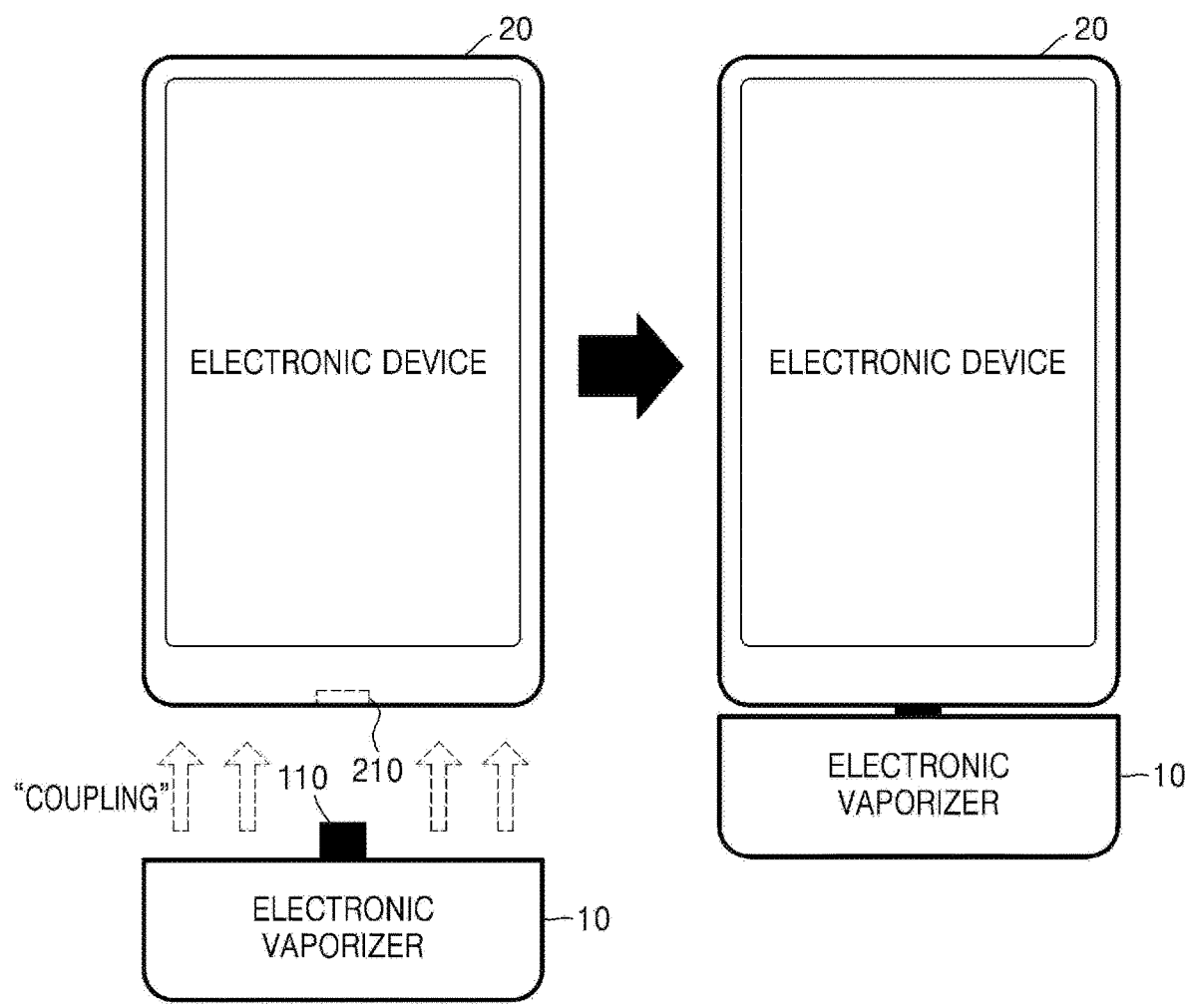
FIG. 1 is a view illustrating an inhalable electronic vaporizer coupled to an electronic device, according to an embodiment.

According to one aspect, an electronic vaporizer for generating an aerosol includes a housing that is coupled to an electronic device by being coupled to the electronic device through a connecting interface of the electronic device, wherein the housing includes a connecting interface that receives power from a battery included in the electronic device when coupled to the connecting interface of the electronic device; a liquid storage for storing a liquid aerosol generating material and supplying the liquid aerosol generating material to a wick when the housing is disposed in a predetermined posture; an atomizer that includes a wick and a heater for generating an aerosol by heating the liquid aerosol generating material supplied to the wick; and a control circuit that controls heating of the heater for generating the aerosol based on the power supplied from the battery.

According to another aspect, an electronic vaporizer for generating an aerosol includes a connecting interface that receives power from a battery included in an electronic device when coupled to a connecting interface of the electronic device; a liquid storage for storing a liquid aerosol generating material and supplying the liquid aerosol generating material to a wick when the electronic vaporizer is disposed in a predetermined posture; an atomizer that includes a wick and a heater for generating an aerosol by heating the liquid aerosol generating material supplied to the wick; a control circuit that controls heating of the heater for generating the aerosol based on the power supplied from the battery; and a mouthpiece that is provided for a user to inhale the aerosol generated from the atomizer.

MODE OF DISCLOSURE

With respect to the terms used to describe the various embodiments, general terms which are currently and widely used are selected in consideration of functions of structural elements in the various embodiments of the present disclosure. However, meanings of the terms can be changed according to intention, a judicial precedence, the appearance of new technology, and the like. In addition, in a certain case, some terms are randomly selected by the applicant, and in this case, meanings thereof will be described in detail in the description of the corresponding disclosure. Accordingly, the terms used in the present disclosure should be defined based on the meanings of the terms and the content of the present disclosure, not simply by the names of the terms.

In addition, unless explicitly described to the contrary, the word "comprise" and variations such as "comprises" or "comprising" will be understood to imply the inclusion of stated elements but not the exclusion of any other elements. In addition, terms such as " . . . portion" and " . . . module" described in the specification mean a unit for processing at least one function or operation, which is implemented by hardware or software or by a combination of the hardware and the software.

Hereinafter, the present disclosure will now be described more fully with reference to the accompanying drawings, in which exemplary embodiments of the present disclosure are shown such that one of ordinary skill in the art may easily work the present disclosure. The disclosure may, however, be embodied in many different forms and should not be construed as being limited to the embodiments set forth herein.

Hereinafter, embodiments of the present disclosure will be described in detail with reference to the drawings.

FIG. 1 is a view illustrating an inhalable electronic vaporizer coupled to an electronic device according to an embodiment.

Referring to FIG. 1, an electronic vaporizer 10 functions as an inhalable aerosol generating device while being combined with an electronic device 20.

The electronic vaporizer 10 may generate an aerosol by heating a liquid aerosol generating material, and the aerosol generated in the electronic vaporizer 10 may be transferred to a user through inhalation of the user.

A liquid aerosol generating material may be stored in the electronic vaporizer 10. For example, the liquid aerosol generating material may include a liquid containing a tobacco material containing a volatile tobacco flavor component, a liquid containing a non-tobacco material, and so on.

For example, the liquid aerosol generating material may include water, solvent, ethanol, plant extracts, fragrance, a flavoring agent, or a vitamin mixture. The fragrance may include menthol, peppermint, spearmint oil, various fruit flavor ingredients, and so on, but is not limited thereto. The flavoring agent may include ingredients that may provide various flavors or savors to a user. The vitamin mixture may be a mixture in which at least one of vitamin A, vitamin B, vitamin C, and vitamin E is mixed, but is not limited thereto. In addition, the liquid composition may include an aerosol former such as glycerin and propylene glycol.

Furthermore, the electronic vaporizer 10 may be referred to as a cartomizer or an atomizer but is not limited thereto and may be referred to as various names.

The electronic device 20 may be a mobile device corresponding to a smartphone, a smartwatch, a tablet PC, a notebook computer (laptop computer), a personal digital assistants (PDA), a portable multimedia player (PMP), a personal digital assistant, and so on, but is not limited thereto.

The electronic device 20 may include a connecting interface 210 for battery charging, connection with a personal computer (PC), and so on. For example, the electronic device 20 may include a Universal Serial Bus (USB) interface as the connecting interface 210, but other types of interfaces may be provided as the connecting interface.

The electronic vaporizer 10, like the electronic device 20, may include a connecting interface 110, for example, a USB interface, but is not limited thereto, and other types of interfaces may be provided. However, it is preferable that the connecting interfaces of the electronic device 20 and the electronic vaporizer 10 are compatible.

The electronic vaporizer 10 may be a device independent of the electronic device 20, as illustrated on the left of FIG. 1. A user may use the electronic vaporizer 10 by coupling to or install in the electronic device 20. Coupling between each other may be completed by inserting the connecting interface 110 of the electronic vaporizer 10 described above into the connecting interface 210 of the electronic device 20. That is, the electronic vaporizer 10 according to the present embodiment is an inhalable device that may be coupled to the electronic device 20. Since, the electronic vaporizer 10 alone has a relatively small volume, the electronic vaporizer 10 may be easily carried. For example, when the electronic device 20 is a smartphone, a length of the electronic vaporizer 10 may be approximately ⅕ of a length of the smartphone. However, this is only an example and the electronic vaporizer 10 may be manufactured in various lengths, various volumes, and so on, which may be ensure portability to a user.

Figure 2:
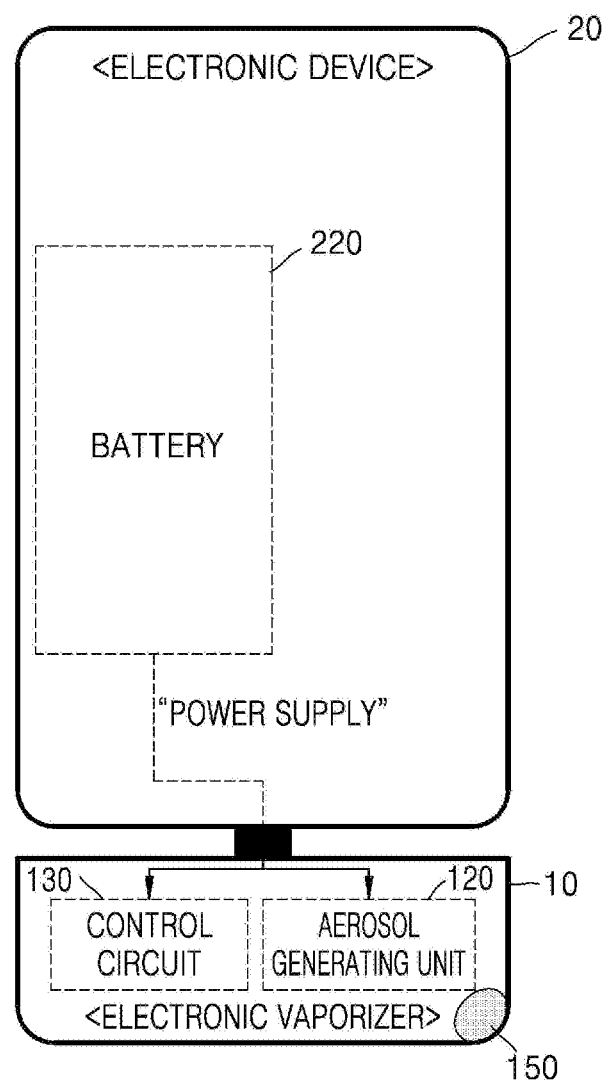
FIG. 2 is a view illustrating an electronic vaporizer coupled to an electronic device, according to an embodiment.

FIG. 2 is a view illustrating an electronic vaporizer mounted in an electronic device according to an embodiment.

Referring to FIG. 2, the electronic device 20 may include a battery 220, and the electronic vaporizer 10 may include an aerosol generating unit 120 and a control circuit 130. However, FIG. 2 illustrates only some elements related to the present embodiment, and those skilled in the art may understand that other general-purpose elements may be further included in each of the electronic vaporizer 10 and the electronic device 20.

The battery 220 of the electronic device 20 supplies power for driving hardware included in the electronic device 20, for example, a central processing unit (CPU), an application processor (AP), various sensors, and so on. Furthermore, the battery 220 may correspond to a battery module with capacity of 2500 mAh or more, but is not limited thereto.

When the electronic vaporizer 10 does not include a separate battery and is coupled to the electronic device 20 through the connecting interfaces 110 and 210, drive power of the electronic vaporizer 10 is supplied from the battery 220 included in the electronic device 20. That is, the aerosol generating unit 120 and the control circuit 130 of the electronic vaporizer 10 are driven by power supplied from the battery 220 of the electronic device 20. Here, power from the battery 220 may be supplied through the connecting interfaces 110 and 210 coupled to each other.

The electronic vaporizer 10 may be manufactured as a housing of a certain size and shape to be coupled to the electronic device 20 through the connecting interface 210 of the electronic device 20, and the housing may include the aerosol generating unit 120 and the control circuit 130. For example, the housing may be manufactured to have a structure that allows close contact with the electronic device 20. The housing is not limited to the shape illustrated in FIG. 2, and it may have various shapes according to a shape of the electronic device 20. A material of the housing may be polymer, urethane, and so on, but is not limited thereto.

The aerosol generating unit 120 heats a liquid aerosol generating material to generate an aerosol. The aerosol generating unit 120 may be manufactured to be detachable from and attachable to the electronic vaporizer 10. Alternatively, the aerosol generating unit 120 may be manufactured integrally with the electronic vaporizer 10. The aerosol generating unit 120 may be referred to as a different term such as a cartridge.

The control circuit 130 is hardware that controls various functions of the electronic vaporizer 10 and may control aerosol generation of the aerosol generating unit 120 based on power supplied from the battery 220. Specifically, the control circuit 130 monitors coupling of the connecting interfaces 110 and 210. When the connecting interfaces 110 and 210 are monitored as being coupled to each other, the control circuit 130 may control a heater of the aerosol generating unit 120 to be heated according to a preset temperature profile by using power supplied from the battery 220.

Furthermore, the control circuit 130 may further include a processor and a memory for controlling and processing various functions of the electronic vaporizer 10, and a wireless communication module for a wireless connection to the electronic device 20 through wireless communication. Here, a method of the wireless communication may be, for example, one or more of various known wireless communication methods, such as Bluetooth, near field communication (NFC), and WI-FI Direct, and so on.

An aerosol generated from the aerosol generating unit 120 may be transferred to a user through a mouthpiece 150 formed on one side of the electronic vaporizer 10.

Figure 3:
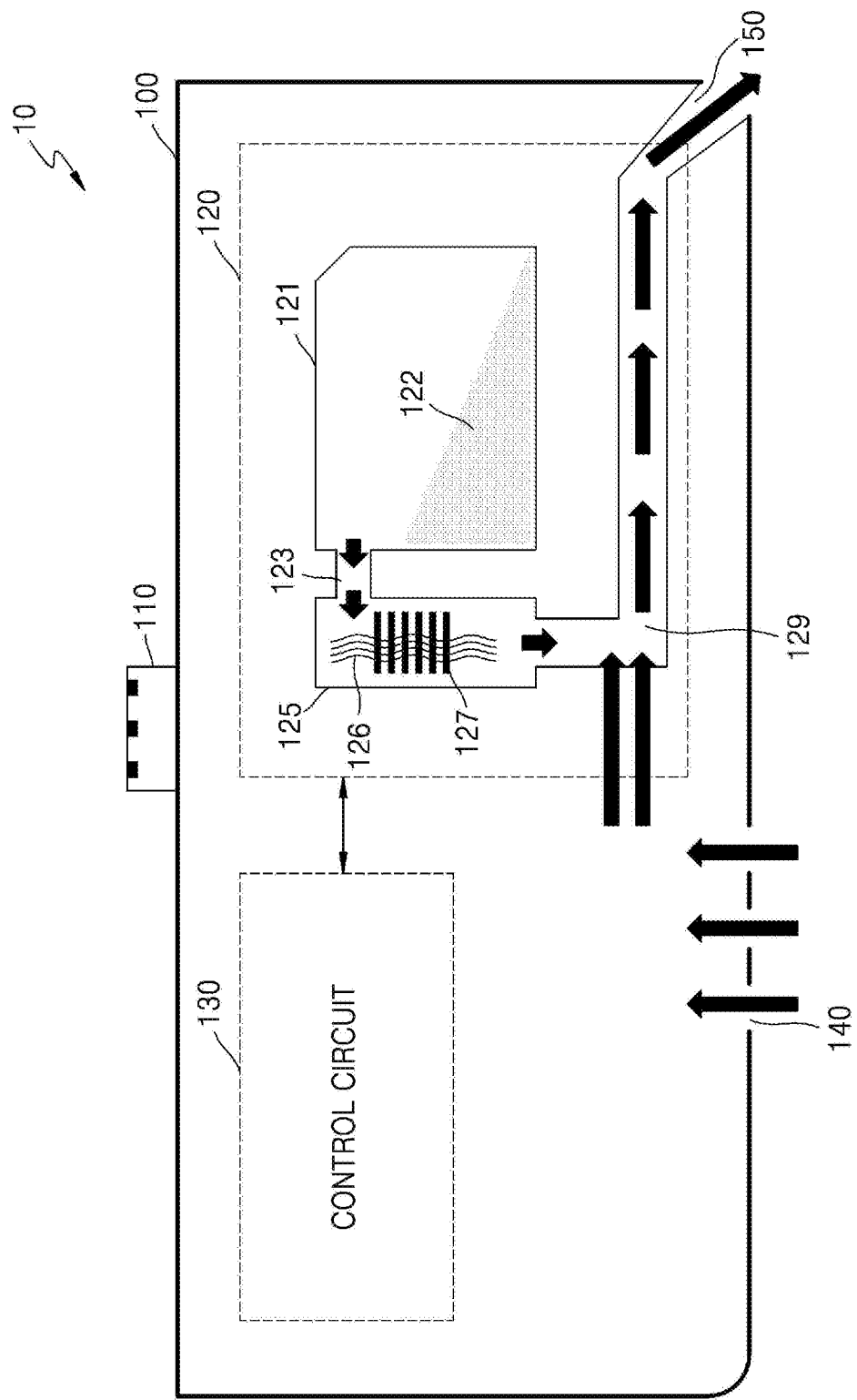
FIG. 3 is a view illustrating an internal structure of an electronic vaporizer according to an embodiment.

FIG. 3 is a view illustrating an internal structure of an electronic vaporizer according to an embodiment.

Referring to FIG. 3, the connecting interface 110 and the control circuit 130 may be included in the housing 100 of the electronic vaporizer 10. In addition, the housing 100 of the electronic vaporizer 10 may also include the aerosol generating unit 120 including a liquid storage 121 and an atomizer 125.

The connecting interface 110 may be a USB port of USB Type-C, micro 5-pin type, or so on, and may be compatible with the connecting interface 210 of the electronic device 20. Power of the battery (220 in FIG. 2) may be supplied from the connecting interface (210 in FIG. 2) of the electronic device (20 in FIG. 2) through the connecting interface 110. However, as described above, the connecting interfaces 110 and 210 may use a different method other than the USB method.

The aerosol generating unit 120 may include a liquid storage 121 and an atomizer 125. The liquid storage 121 stores the liquid aerosol generating material 122 and supplies the liquid aerosol generating material 122 to a wick 126 when the housing 100 is disposed in a predetermined posture. The atomizer 125 includes a wick 126 and a heater 127 that generates an aerosol by heating the liquid aerosol generating material 122 supplied to the wick 126.

The liquid storage 121 of the aerosol generating unit 120 is a container or a tank for storing the liquid aerosol generating material 122 therein. The liquid storage 121 may store, for example, an amount of the liquid aerosol generating material 122 that allows a user to puff approximately 100 to 200 times.

According to the present embodiment, the liquid storage 121 may sufficiently supply the liquid aerosol generating material 122 to the wick 126 only when the housing 100 is disposed in a predetermined posture, and may block supply of the liquid aerosol generating material 122 when the housing 100 is not disposed in the predetermined posture. Here, the housing 100 may be disposed in the predetermined posture when a user holds the electronic vaporizer 10 and the electronic device 20, which are coupled to each other, such that the electronic vaporizer 10 is located above the electronic device 20. That is, the housing 100 may be disposed in the predetermined posture when the user holds the electronic device 20 upside down while the electronic device 20 and the electronic vaporizer 10 are coupled to each other. However, this posture is described on the assumption that the connecting interface 210 of the electronic device 20 is located at the bottom, and thus, those skilled in the art may understand that, when the connecting interface 210 is located at another place other than the bottom in the electronic device 20, the predetermined posture may vary. Furthermore, the housing 100 may be disposed in the predetermined posture not only strictly when a user holds the electronic vaporizer 10 to be located above the electronic device 20, but also when the housing 100 is slightly inclined.

The wick 126 included in the atomizer 125 of the aerosol generating unit 120 may transfer the liquid aerosol generating material 122 supplied from the liquid storage 121 to the heater 127. For example, the wick 126 may include a material such as cotton fiber, ceramic fiber, glass fiber, or porous ceramic, but is not limited thereto.

The heater 127 included in the atomizer 125 of the aerosol generating unit 120 may heat the liquid aerosol generating material 122 transferred to the wick 126. For example, the heater 127 may be a metal heating wire, a metal heating plate, a ceramic heater, a coil heater, or a mesh heater, but is not limited thereto. The heater 127 may be wound around the wick 126 and may be embodied as a conductive filament such as a nichrome wire. The heater 127 may be heated by power supplied from a battery (220 of FIG. 2). Heat may be transferred to the liquid aerosol generating material 122 in contact with the heater 127 to heat the liquid aerosol generating material 122, and as a result, an aerosol may be generated.

The aerosol generating unit 120 may include a connection path 123 through which the liquid aerosol generating material 122 is provided to the atomizer 125 when the housing 100 is disposed in a predetermined posture. The liquid aerosol generating material 122 is not provided to the atomizer 125 when the housing 100 is not disposed in the predetermined posture.

The housing 100 may include at least one hole 140 through which external air is introduced into the housing, and an airflow path 129 through which a mixture of the external air introduced through the hole 140 and the generated aerosol is provided to the mouthpiece 150.

The control circuit 130 controls various functions of the electronic vaporizer 10 as described above with reference to FIG. 2. For example, the control circuit 130 may control an aerosol generating function and so on, by controlling a temperature of the heater 127 of the atomizer 125.

Furthermore, FIG. 3 illustrates only some elements related to the present embodiment, and those skilled in the art will understand that the electronic vaporizer 10 may further include other general-purpose elements.

Figure 4:
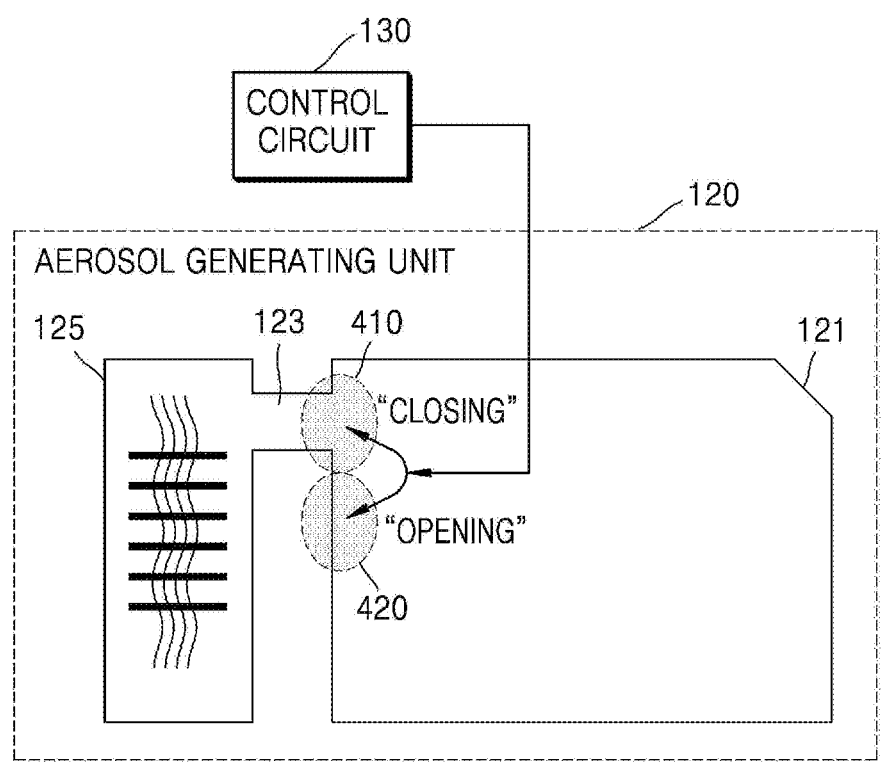
FIG. 4 is a view illustrating a connection path between a liquid storage and an atomizer, according to an embodiment.

FIG. 4 is a view illustrating a connection path between the liquid storage and the atomizer, according to an embodiment.

Referring to FIG. 4, the connection path 123 located between the liquid storage 121 and the atomizer 125 in the aerosol generating unit 120 is a path through which a liquid aerosol material stored in the liquid storage 121 is supplied to the atomizer 125.

The electronic vaporizer 10 according to this embodiment may not generate an aerosol while it is not coupled to the electronic device 20. Accordingly, while the electronic vaporizer 10 is not coupled to the electronic device 20, the liquid aerosol material does not have to be supplied to the atomizer 125. However, it is difficult for a user of the electronic vaporizer 10 to carry the electronic vaporizer 10 in a specific posture, and thus, there is a possibility that the liquid aerosol generating material of the liquid storage 121 unintentionally overflows to be transferred to the atomizer 125 through the connection path 123.

In order to prevent the liquid aerosol generating material from being unintentionally transferred, a blocking stopper may be provided between the liquid storage 121 and the connection path 123. In the state 410, the blocking stopper is closed such that the liquid aerosol generating material is blocked and not transmitted to the atomizer 125 from the liquid storage 121. In the state 420, the blocking stopper is opened such that the liquid aerosol generating material may be transferred from the liquid storage 121 to the atomizer 125.

The control circuit 130 may control an opening and closing operations of the blocking stopper. Specifically, the control circuit 130 may monitor whether or not the connecting interface 210 of the electronic device 20 is coupled to the connecting interface 110 of the housing 100. When the connecting interfaces 110 and 210 are monitored as being coupled to each other, the control circuit 130 may control the blocking stopper to be in the open state 420 so that the connection path 123 is opened. When the connection interfaces 110 and 210 are monitored as not being connected to each other, the control circuit 130 may control the blocking stopper to be in the closed state 410 so that the connection path 123 is closed.

Furthermore, the blocking stopper may correspond to a mechanical element that mechanically operates based on a switching signal of the control circuit 130, but is not limited thereto.

Figure 5A:
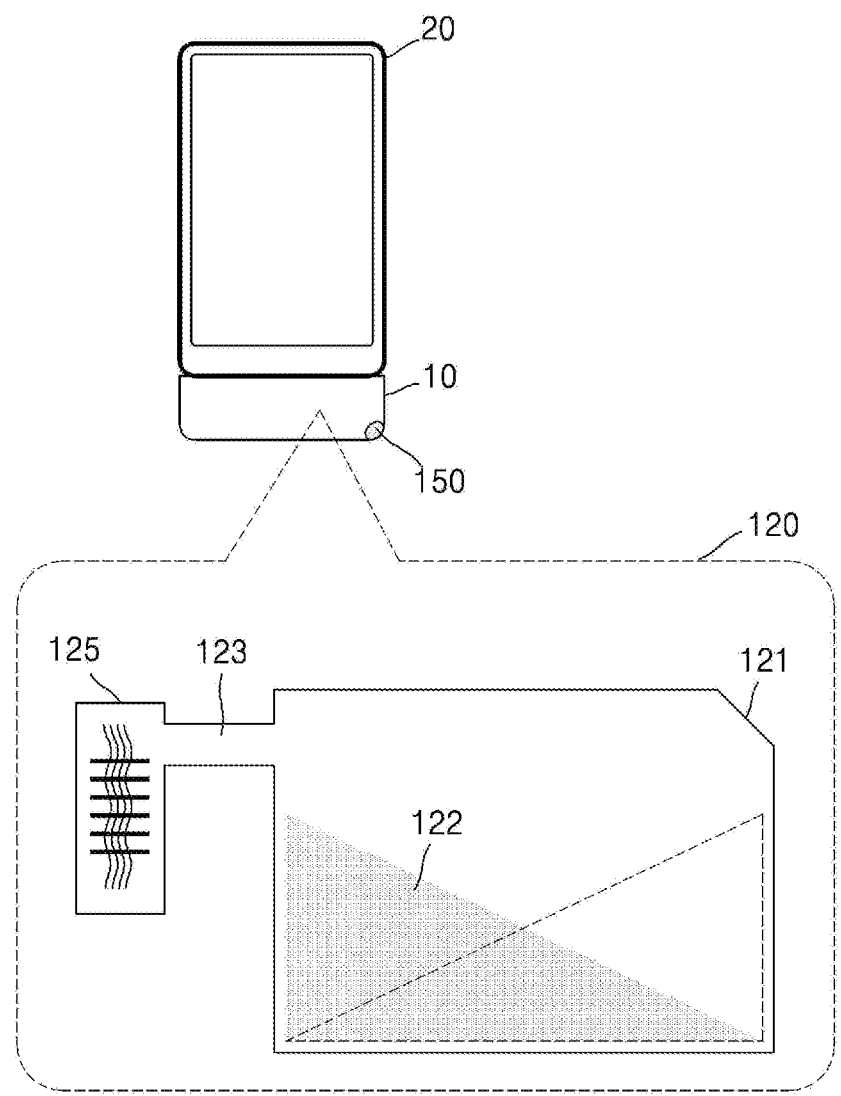
FIGS. 5A and 5B are views illustrating a state of a liquid aerosol generating material in a liquid storage when an electronic vaporizer coupled to an electronic device is not disposed in a predetermined posture according to an embodiment.
Figure 5B:
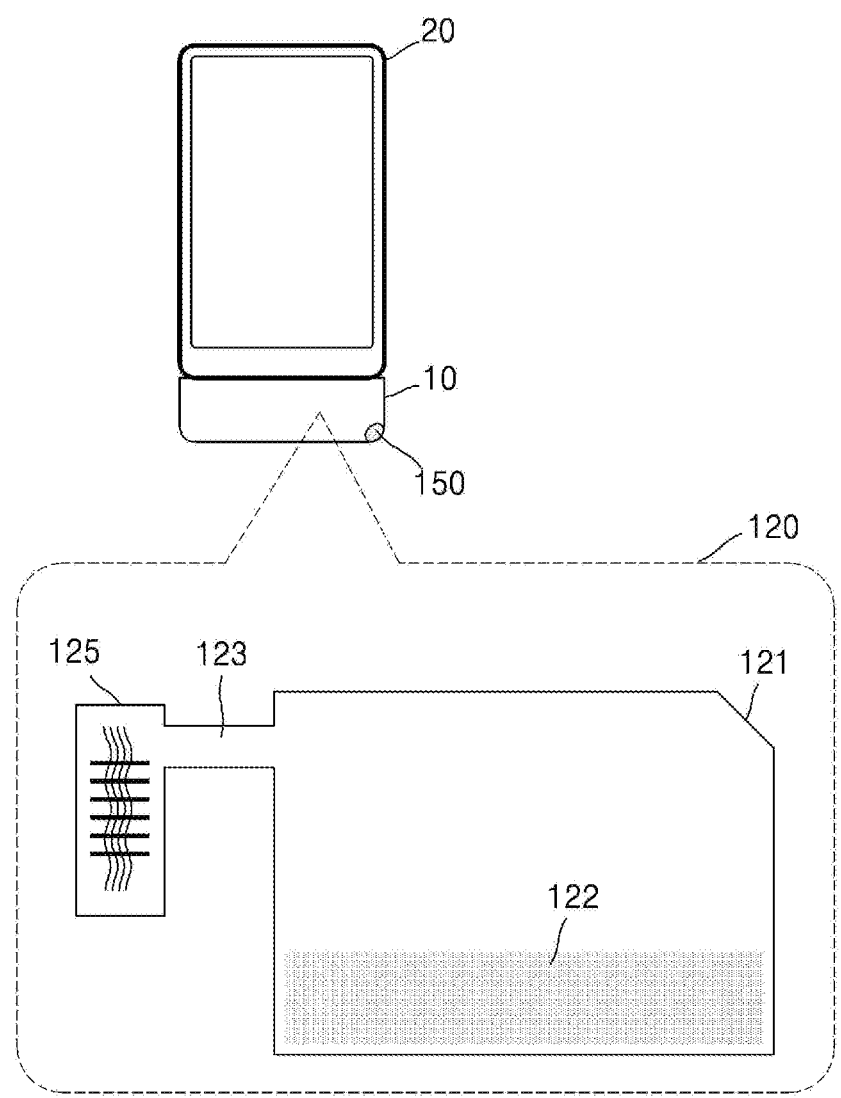

FIGS. 5A and 5B are views illustrating a state of a liquid aerosol generating material in a liquid storage when an electronic vaporizer coupled to an electronic device is not disposed in a predetermined posture, according to an embodiment.

Referring to FIGS. 5A and 5B, the electronic vaporizer 10 coupled to the electronic device 20 is not disposed in the predetermined posture described above. That is, FIGS. 5A and 5B illustrate states in which the electronic device 20 is located above the electronic vaporizer 10.

In this case, the liquid aerosol generating material 122 is not transferred to the atomizer 125 in the aerosol generating unit 120 of the electron vaporizer 10. Specifically, in the embodiments of FIGS. 5A and 5B, the liquid aerosol generating material 122 in the liquid storage 121 does not enter the connection path 123 but only sways on a bottom portion of the liquid storage 121. Therefore, even if the electronic device 20 and the electronic vaporizer 10 are coupled to each other, an aerosol is not generated unless the electronic vaporizer 10 is disposed in a predetermined posture.

Figure 6:
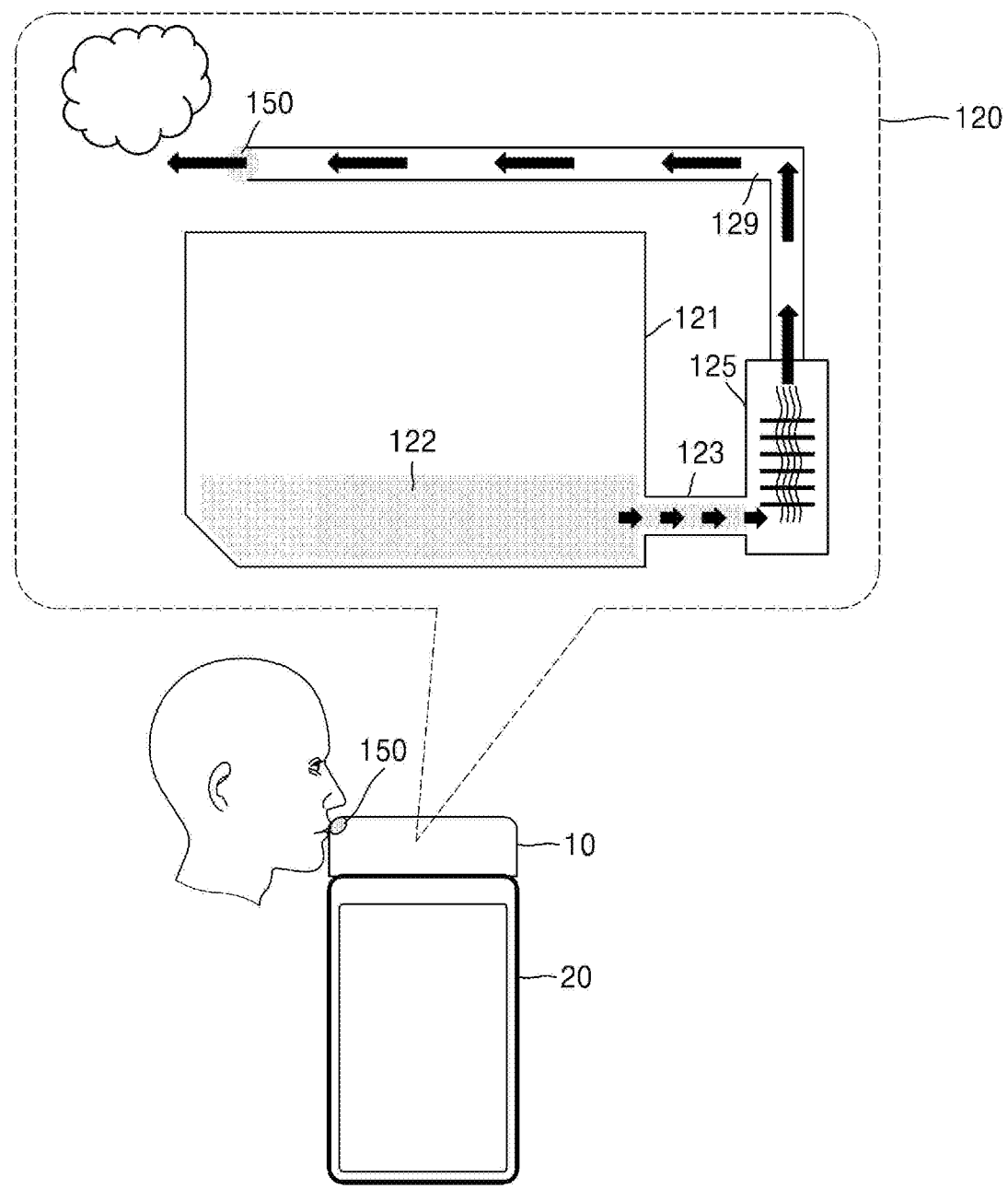
FIG. 6 is a view illustrating that an aerosol is generated and transferred to a mouthpiece when an electronic vaporizer coupled to an electronic device is disposed in a predetermined posture according to an embodiment.

FIG. 6 is a view illustrating that an aerosol is generated and transferred to a mouthpiece when an electronic vaporizer coupled to an electronic device is disposed in a predetermined posture, according to an embodiment.

Referring to FIG. 6, unlike FIGS. 5A and 5B, the electronic vaporizer 10 coupled to the electronic device 20 is disposed in a predetermined posture described above. That is, a user is holding the electronic device 20 upside down, and the electronic vaporizer 10 is located above the electronic device 20.

In this case, the liquid aerosol generating material 122 in the liquid storage 121 is located on the bottom portion connected to the connection path 123, and thus, the liquid aerosol generating material 122 is supplied to the atomizer 125 through the connection path 123. The liquid aerosol generating material 122 supplied to the atomizer 125 is transferred to a wick. A heater surrounding the wick in the atomizer 125 is heated by power supplied from the battery (220 in FIG. 2), and the heat is transferred to the liquid aerosol generating material 122 in contact with the heater. As a result, the liquid aerosol generating material 122 is heated and an aerosol may be generated.

The generated aerosol passes through an airflow path 129 to be mixed with external air and may be transferred to a user through the mouthpiece 150.

That is, in the electronic vaporizer 10 according to the present embodiment, the aerosol generating unit 120 has a structure in which the liquid aerosol generating material 122 may be sufficiently supplied to the atomizer 125 to generate an aerosol only while the electron vaporizer 10 (or the housing (100 of FIG. 3)) is disposed in a predetermined posture. Thus, leakage of the liquid aerosol generating material 122 may be minimized when a user uses, keeps, or carries the electronic vaporizer 10.

Figure 7:
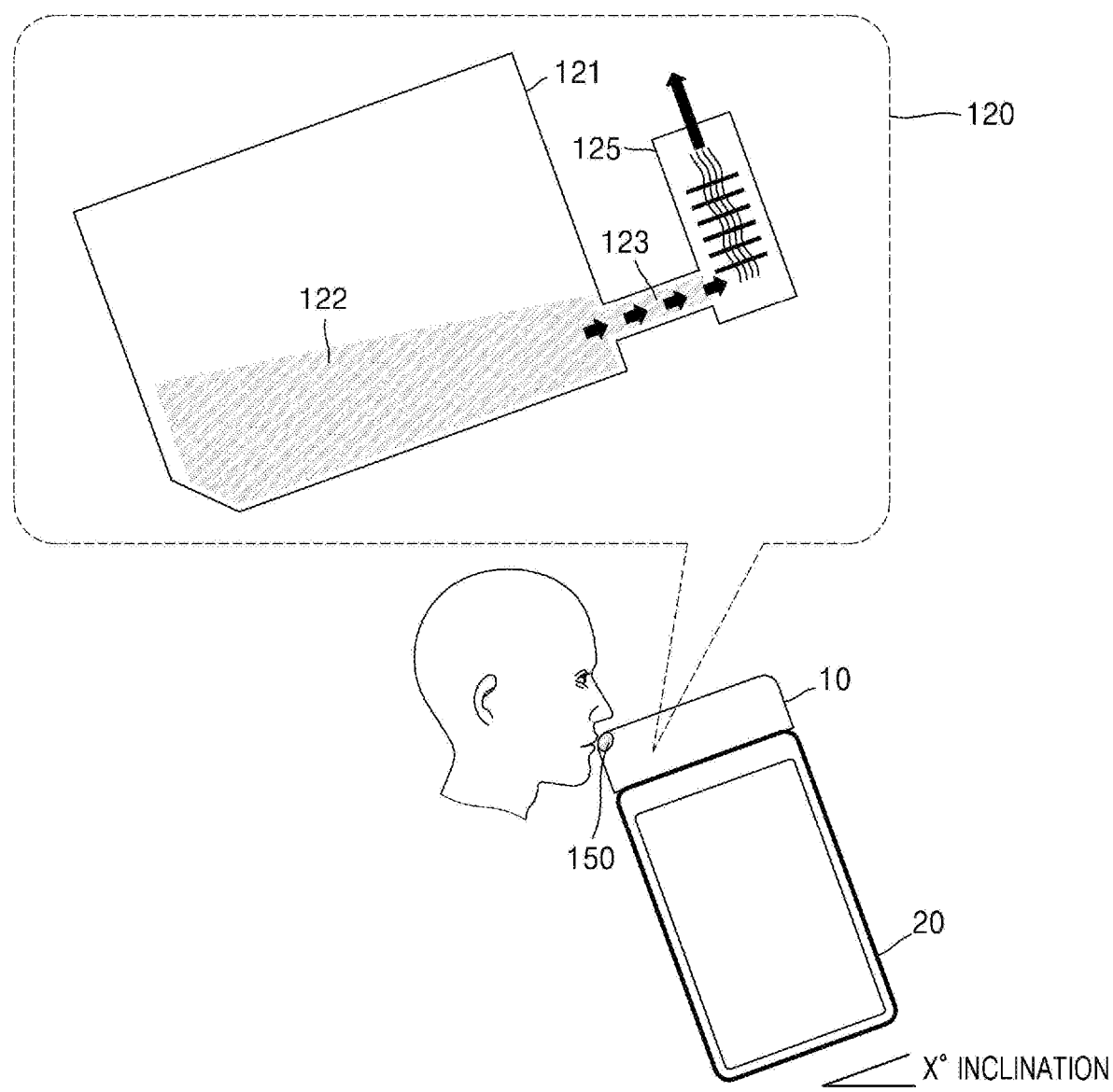
FIG. 7 is a view illustrating that an aerosol is generated and transferred to a mouthpiece when an electronic vaporizer coupled to an electronic device is disposed in a predetermined posture according to another embodiment.

FIG. 7 is a view illustrating that an aerosol is generated and transferred to a mouthpiece when an electronic vaporizer coupled to an electronic device is disposed in a predetermined posture, according to another embodiment.

Referring to FIG. 7, a user may use the electronic vaporizer 10 while holding the electronic device 20 coupled to the electronic vaporizer 10 upside down such that the electronic vaporizer 10 is slightly inclined at a predetermined slope.

As described in FIG. 6, the liquid aerosol generating material 122 in the liquid storage 121 is located on the bottom portion connected to the connection path 123 and supplied to the atomizer 125 through the connection path 123. The liquid aerosol generating material 122 supplied to the atomizer 125 may be transferred to a wick, and an aerosol may be generated by heating the heater. A user may inhale the aerosol coming out of the mouthpiece 150 by biting the mouthpiece 150.

As described in FIGS. 5A to 7, when the electronic vaporizer 10 (that is, the housing 100 of the electronic vaporizer 10) coupled to the electronic device 20 is disposed in a predetermined posture such that the liquid aerosol generating material 122 in in the liquid storage 121 may be sufficiently supplied to the atomizer 125 through the connection path 123, a user may inhale the aerosol by using the electronic vaporizer 10. However, when the electronic vaporizer 10 is disposed in a posture in which the liquid aerosol generating material 122 in the liquid storage 121 may not be sufficiently supplied to the atomizer 125 through the connection path 123, it is difficult for a user to inhale the aerosol by using the electronic vaporizer 10.

That is, those skilled in the art may understand that, in the embodiments, a predetermined posture may be defined based on a posture of the electron vaporizer 10 (i.e., a posture of the housing 100 of the electron vaporizer 10).

Figure 8A:
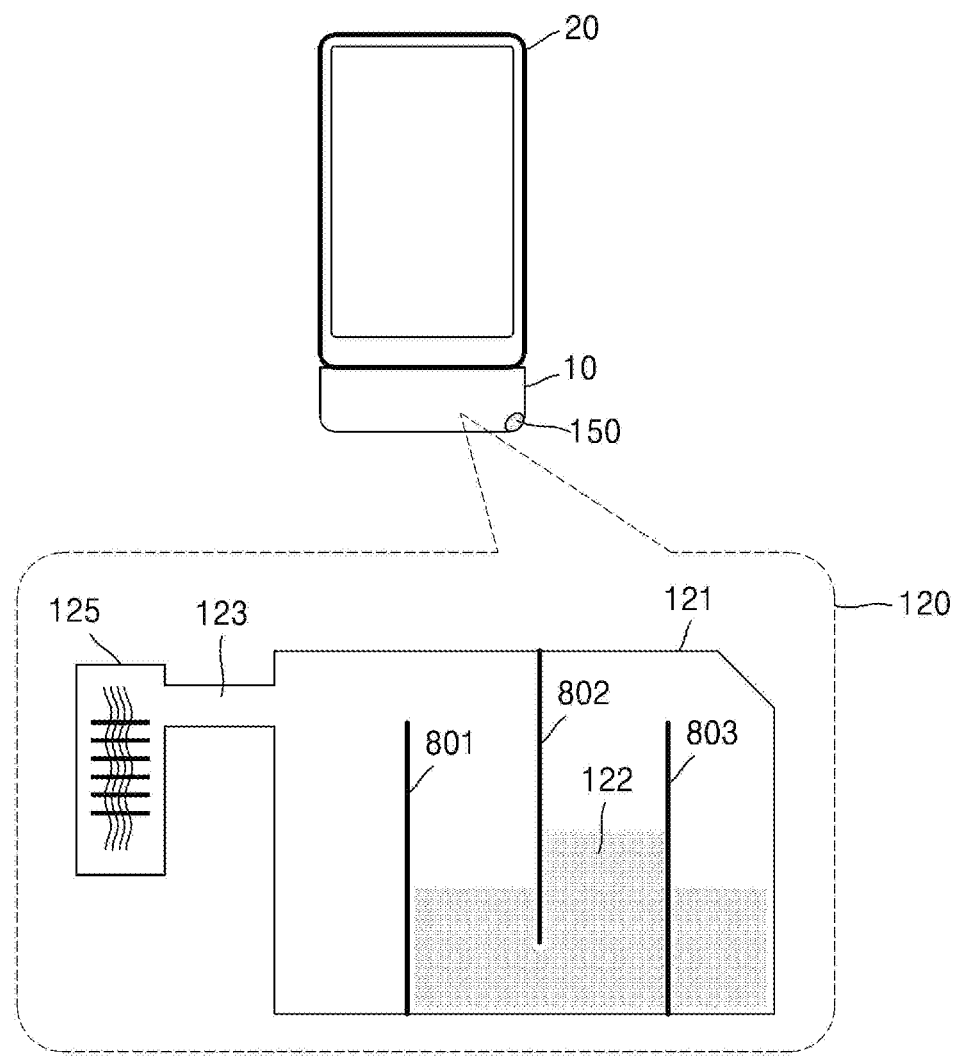
FIGS. 8A and 8B are views illustrating an internal structure of a liquid storage according to another embodiment.
Figure 8B:
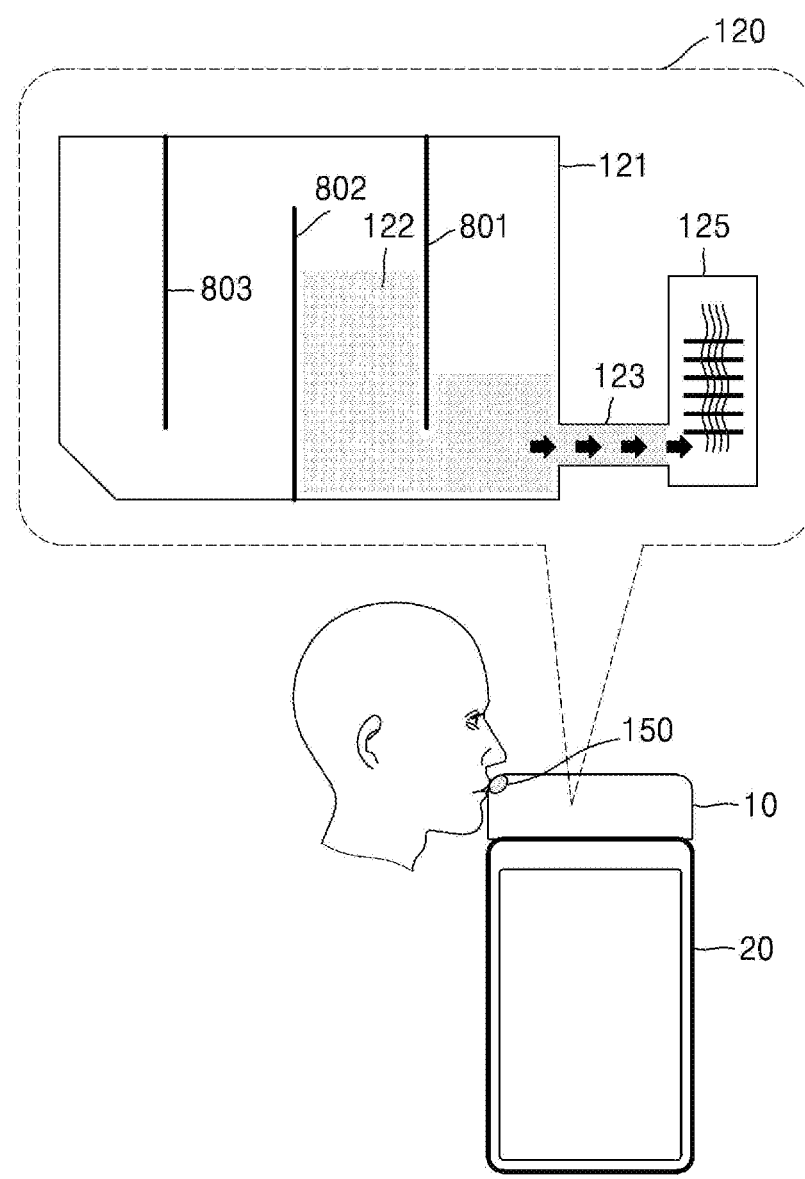

FIGS. 8A and 8B are views illustrating an internal structure of a liquid storage according to another embodiment.

Referring to FIGS. 8A and 8B, the liquid storage 121 may include one or more wall surfaces 801, 802, and 803 that partition an inner space of the liquid storage 121 for storing the liquid aerosol generating material 122.

The wall surfaces 801, 802, and 803 may have a structure that provides the liquid aerosol generating material 122 to the atomizer 125 when the housing 100 of the electronic vaporizer 10 is disposed in a predetermined posture as illustrated in FIG. 8B, and does not provide the liquid aerosol generating material 122 to the atomizer 125 when the housing 100 is not disposed in the predetermined posture as illustrated in FIG. 8A.

Figure 9:
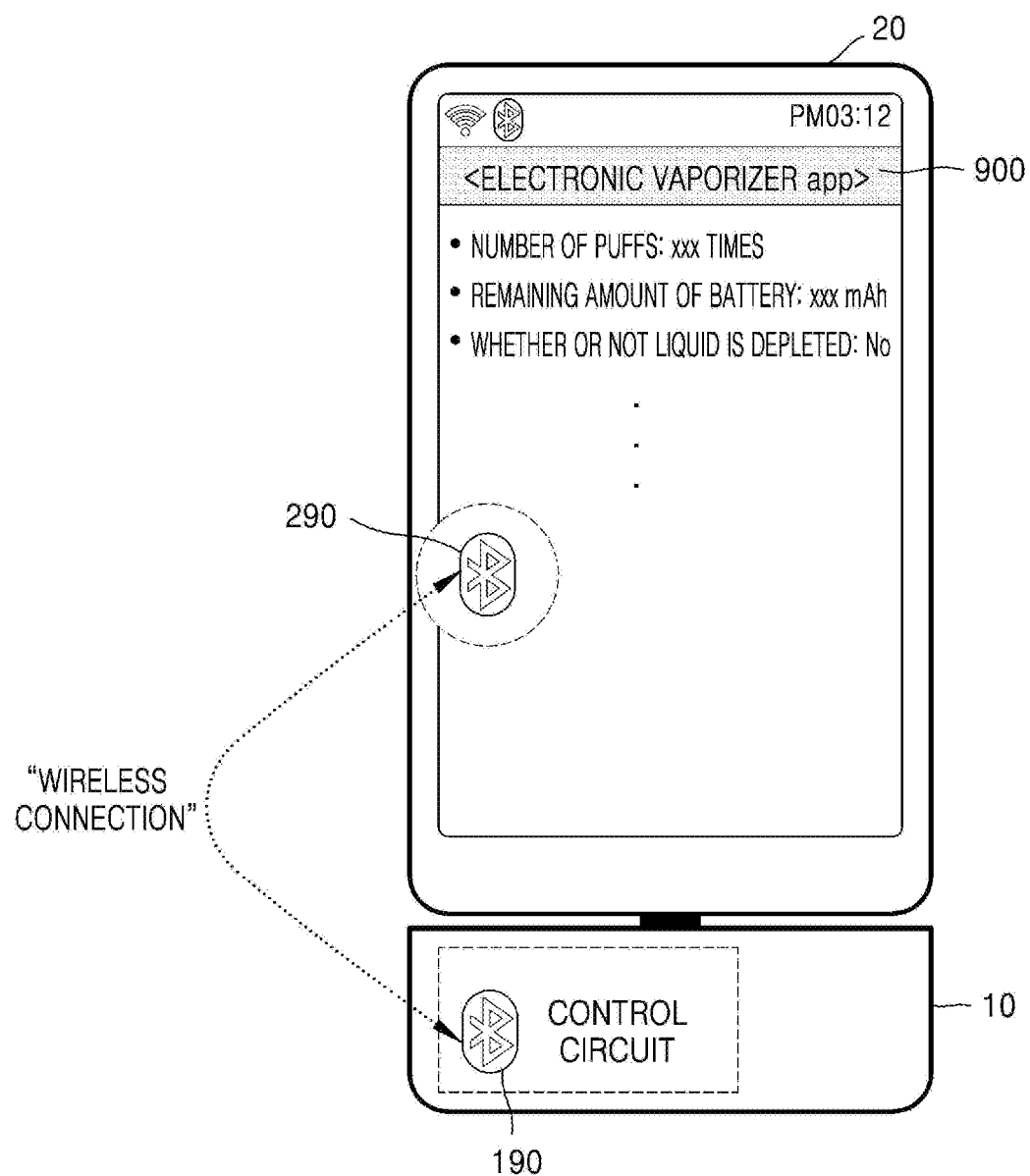
FIG. 9 is a view illustrating that an electronic vaporizer is controlled by using an electronic device according to an embodiment.

FIG. 9 is a view illustrating that an electronic vaporizer is controlled by using an electronic device, according to an embodiment.

Referring to FIG. 9, when the electronic vaporizer 10 is coupled to the electronic device 20, a wireless connection may be established between the electronic vaporizer 10 and the electronic device 20 through wireless communication. For example, a wireless connection between the electronic vaporizer 10 and the electronic device 20 may be established through Bluetooth.

A vaporizer control application 900 for controlling the electronic vaporizer 10 may be executed in the electronic device 20. The control circuit 130 of the electronic vaporizer 10 controls operations of the electronic vaporizer 10 under the control of the vaporizer control application 900.

For example, when the vaporizer control application 900 is executed in the electronic device 20, the vaporizer control application 900 may provide information such as the number of puffs performed in the electronic vaporizer 10, the remaining power of a battery of the electronic device 20 which drives the electronic vaporizer 10, depletion the liquid aerosol generating material 122 in the liquid storage 121, a heater temperature, etc. In addition, a user may configure various settings of the electronic vaporizer 10 through the vaporizer control application 900, such as a range of a heater temperature, and a notification mode such as vibration/sound/display, etc.

That is, when a wireless connection with a wireless communication module 290 of the electronic device 20 is established, a wireless communication module 190 of the electronic device 10 may receive data set in the vaporizer control application 900 executed by the electronic device 20 or may transmit data requested from the vaporizer control application 900.

Those of ordinary skill in the art related to the present embodiments may understand that various changes in form and details can be made therein without departing from the scope of the characteristics described above. The disclosed methods should be considered in a descriptive sense only and not for purposes of limitation. The scope of the present disclosure is represented in the claims rather than the foregoing description, and all differences within the equivalent range should be interpreted as being included in the present disclosure.

What is claimed is:

1. An electronic vaporizer for generating an aerosol, comprising:
   a housing configured to be installed to a portion of an electronic device by being physically coupled to the electronic device through a connecting interface of the electronic device at the portion of the electronic device, the housing comprising:
   a connecting interface at a first side of the housing in a first direction, the connecting interface configured to receive power from a battery included in the electronic device when physically coupled to the connecting interface of the electronic device;
   a liquid storage configured to store a liquid aerosol generating material, supply the liquid aerosol generating material to a wick based on the housing being disposed in a first predetermined posture, and not supply the liquid aerosol generating material to the wick based on the housing being disposed in a second predetermined posture;
   an atomizer including the wick and a heater that generates the aerosol by heating the liquid aerosol generating material supplied to the wick; and
   a control circuit configured to control heating of the heater for generating the aerosol based on the power supplied from the battery,
   wherein the first predetermined posture is a posture in which the first side of the housing faces downwards based on the electronic device being oriented such that the housing is above the electronic device and the portion of the electronic device faces upwards while the housing is installed to the portion of the electronic device, and
   wherein the second predetermined posture is a posture in which the first side of the housing faces upwards based on the electronic device being oriented such that the housing is below the electronic device and the portion of the electronic device faces downwards while the housing is installed to the portion of the electronic device.

2. The electronic vaporizer of claim 1, wherein the liquid storage includes a connection path through which the liquid aerosol generating material is provided to the atomizer when the housing is disposed in the first predetermined posture, and through which the liquid aerosol generating material is not provided to the atomizer when the housing is not disposed in the second predetermined posture.

3. The electronic vaporizer of claim 2, wherein the control circuit is further configured to:
   monitor whether or not the connecting interface of the electronic device is physically coupled to the connecting interface of the housing;
   control the connection path to be opened when the connecting interface of the of the electronic device and the connecting interface of the electronic vaporizer are physically coupled to each other; and
   control the connection path to be closed when the connecting interface of the of the electronic device and the connecting interface of the electronic vaporizer are not physically coupled to each other.

4. The electronic vaporizer of claim 2, wherein the connection path extends outwards from a portion of an outer wall of the liquid storage,
   wherein the outer wall extends in a second direction intersecting and non-parallel with the first direction, and
   wherein the portion of the outer wall is closer to a first side of the housing in the first direction than a second side of the housing, opposite to the first side.

5. The electronic vaporizer of claim 1, wherein the housing further comprises a mouthpiece provided on one side of the housing for a user to inhale the aerosol generated from the atomizer, and
   wherein the mouthpiece is configured to provide the aerosol to the user when the housing is disposed in the first predetermined posture.

6. The electronic vaporizer of claim 5, wherein the housing comprises:
   at least one hole that introduces external air into the housing; and
   an airflow path through which a mixture of the external air and the aerosol is provided to the mouthpiece.

7. The electronic vaporizer of claim 5, wherein an outlet of the mouthpiece is at least partially on a side of the housing that faces in a second direction that intersects and is non-parallel with the first direction.

8. The electronic vaporizer of claim 1, wherein the housing further comprises a wireless communication module for establishing a wireless connection with the electronic device through wireless communication.

9. The electronic vaporizer of claim 8, wherein the wireless communication module receives data set in a vaporizer control application executed by the electronic device or transmits data requested from the vaporizer control application through the wireless connection established with the electronic device, and
   wherein the control circuit controls operations of the electronic vaporizer under control of the vaporizer control application.

10. The electronic vaporizer of claim 1, wherein the liquid storage includes one or more wall surfaces that partition an inner space of the liquid storage for storing the liquid aerosol generating material, and
    wherein the one or more wall surfaces are disposed in a structure that provides the liquid aerosol generating material to the atomizer when the housing is disposed in the first predetermined posture, and does not provide the liquid aerosol generating material to the atomizer when the housing is disposed in the second predetermined posture.

11. The electronic vaporizer of claim 1, wherein the electronic vaporizer does not include a battery.

12. An electronic vaporizer for generating an aerosol, comprising:
    a connecting interface at a first side of the electronic vaporizer in a first direction, the connecting interface configured to receive power from a battery included in an electronic device when physically coupled to a connecting interface of the electronic device that is at a portion of the electronic device;

a liquid storage configured to store a liquid aerosol generating material, supply the liquid aerosol generating material to a wick based on the electronic vaporizer being disposed in a first predetermined posture, and not supply the liquid aerosol generating material to the wick based on the electronic vaporizer being disposed in a second predetermined posture;

an atomizer that includes the wick and a heater configured to generate the aerosol by heating the liquid aerosol generating material supplied to the wick;

a control circuit configured to control heating of the heater for generating the aerosol, based on the power supplied from the battery; and a mouthpiece through which the aerosol generated from the atomizer is inhaled by a user, wherein the first predetermined posture is a posture in which the first side of the electronic vaporizer faces downwards based on the electronic device being oriented such that the electronic vaporizer is above the electronic device and the portion of the electronic device faces upwards while the electronic vaporizer is installed to the portion of the electronic device, and wherein the second predetermined posture is a posture in which the first side of the electronic vaporizer faces upwards based on the electronic device being oriented such that the electronic vaporizer is below the electronic device and the portion of the electronic device faces downwards while the housing is installed to the portion of the electronic device.

\* \* \* \* \*